United States Patent [19]
Schohe-Loop et al.

[11] Patent Number: 5,942,529
[45] Date of Patent: *Aug. 24, 1999

[54] BENZISOTHIAZOLYL-SUBSTITUTED AMINOMETHYLCHROMANS

[75] Inventors: Rudolf Schohe-Loop, Wuppertal; Hans-Georg Heine, Krefeld; Peter-Rudolf Seidel, Köln; Wolfgang Kanhai; Joachim Schuhmacher, both of Wuppertal; Arno Friedl, Bergisch Gladbach; Ervin Horvath, Leverkusen; Thomas Glaser; Reinhard Jork, both of Overath, all of Germany

[73] Assignee: Bayer Aktiengesellschaft, Leverkusen, Germany

[21] Appl. No.: 08/663,398

[22] Filed: Jun. 13, 1996

[30] Foreign Application Priority Data

Jun. 19, 1995 [DE] Germany ............. 195 22 088

[51] Int. Cl.$^6$ ............. C07D 417/00; A61K 31/425
[52] U.S. Cl. ............. 514/373; 548/207; 548/208; 548/210
[58] Field of Search ............. 548/210; 514/373

[56] References Cited

U.S. PATENT DOCUMENTS

| | | | |
|---|---|---|---|
| 5,049,588 | 9/1991 | Nicholson et al. | 514/657 |
| 5,137,901 | 8/1992 | Junge et al. | 514/373 |
| 5,252,578 | 10/1993 | Guillaumet et al. | 514/278 |
| 5,300,523 | 4/1994 | Junge et al. | 514/456 |
| 5,314,907 | 5/1994 | Guillaumet et al. | 514/414 |
| 5,318,988 | 6/1994 | Schohe-Loop et al. | 514/458 |
| 5,326,771 | 7/1994 | Heine et al. | 514/316 |
| 5,346,916 | 9/1994 | Guillaumet et al. | 514/434 |
| 5,364,857 | 11/1994 | Bode-Greuel | 514/259 |
| 5,468,882 | 11/1995 | Schohe-Loop et al. | 549/407 |
| 5,506,246 | 4/1996 | Junge et al. | 514/373 |
| 5,510,374 | 4/1996 | Guillamet et al. | 514/456 |

FOREIGN PATENT DOCUMENTS

| | | |
|---|---|---|
| 0 352 613 A2 | 1/1990 | European Pat. Off. . |
| 0 539 803 A1 | 5/1993 | European Pat. Off. . |
| 0 540 914 A1 | 5/1993 | European Pat. Off. . |

OTHER PUBLICATIONS

Millan et al. "The Journal of Pharmacology + Experimental Therapeutics", 262, No. 2, pp. 451–463 (1992).

J.B. Bederson et al., Stroke, vol. 17, No. 3, pp. 472–476 (1986).

W.V. Dompert et al., Arch.Pharmacol., vol. 328, pp. 467–470 (1985).

Primary Examiner—Jose' G. Dees
Assistant Examiner—Sabiha Qazi
Attorney, Agent, or Firm—Sprung Kramer Schaefer & Briscoe

[57] ABSTRACT

The benzisothiazolyl-substituted aminomethylchromans are prepared either by substituting the corresponding unsubstituted aminomethylchromans on the amine nitrogen or reacting the corresponding benzisothiazolylalkylamines with appropriate activated methylchromans or reacting the amine nitrogen of aminomethylchroman first with an appropriately substituted alkine and then hydrogenating. The benzisothiazolyl-substituted aminomethylchromans can be used as active compounds in medicaments, in particular in medicaments for the treatment of disorders of the central nervous system.

6 Claims, No Drawings

BENZISOTHIAZOLYL-SUBSTITUTED AMINOMETHYLCHROMANS

The present invention relates to benzisothiazolyl-substituted aminomethylchromans, processes for their preparation and their use in medicaments, in particular as agents for controlling disorders of the central nervous system.

The publications EP 352 613 and EP 540 914 disclose aminotetralin and chroman derivatives having CNS activity.

The invention relates to new benzisothiazolyl-substituted aminomethylchromans of the general formula (I)

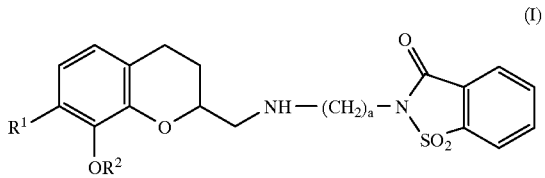

in which

R$^1$ represents hydrogen, and

R$^2$ represents a radical of the formula —CH(CH$_3$)$_2$ or —CH$_2$—C(CH$_3$)$_2$—Cl, or R$^1$ and R$^2$ together form a radical of the formula

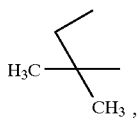

and a represents a number 3, 4 or 5, if appropriate in an isomeric form, and their salts.

Surprisingly, the compounds according to the invention show good activity in the treatment of damage as a result of cerebral infarcts.

In the context of the present invention, physiologically acceptable salts are preferred. Physiologically acceptable salts of the benzisothiazolyl-substituted aminomethylchromans can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

In the context of the present invention, the compounds according to the invention can be present in various stereoisomeric forms. The compounds according to the invention exist in stereoisomeric forms which behave either as image and mirror image (enantiomers), or which do not behave as image and mirror image (diastereomers). The invention relates both to the antipodes and to the racemic forms as well as the diastereomer mixtures. Like the diastereomers, the racemic forms can be separated into the stereoisomerically uniform constituents in a known manner.

For example, the following isomers may be mentioned:

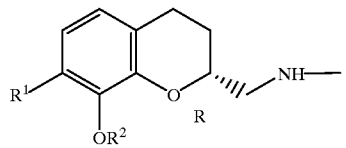

(A)

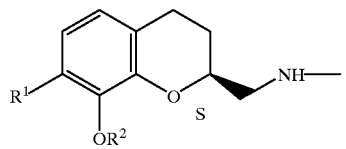

(B)

Preferred compounds of the general formula (I) are those in which

R$^1$ represents hydrogen, and

R$^2$ represents a radical of the formula —CH(CH$_3$)$_2$ or —CH$_2$—C(CH$_3$)$_2$—Cl, or R$^1$ and R$^2$ together form a radical of the formula

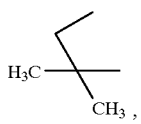

and a represents a number 3 or 4, if appropriate in an isomeric form, and their salts.

Particularly preferred compounds of the genial formula (I) are those in which

R$^1$ represents hydrogen, and

R$^2$ presents a radical of the formula —CH(CH$_3$)$_2$ or —CH$_2$—C(CH$_3$)$_2$—Cl, or R$^1$ and R$^2$ together form a radical of the formula

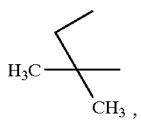

and a represents the number 4, if appropriate in an isomeric form, and their salts.

The benzisothiazolyl-substituted aminomethylchromans according to the invention are prepared by

[A] reacting amines of the general formula (II)

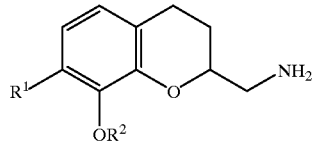

in which

R$^1$ and R$^2$ have the meaning indicated above, with compounds of the general formula (III)

(III)

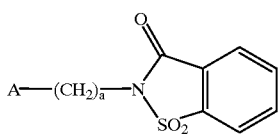

in which

A represents a typical leaving group such as chlorine, bromine, iodine, tosylate, mesylate or the group —OSO$_2$CF$_3$, and a has the meaning indicated above, in inert solvents, if appropriate in the presence of a base, or

[B] reacting compounds of the general formula (IV)

(IV)

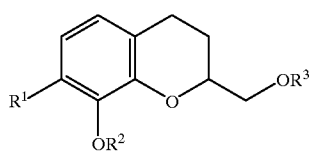

in which

R$^1$ and R$^2$ have the meaning indicated above and

R$^3$ represents a radical of the formula —SO$_2$CF$_3$, —SO$_2$CH$_3$ or tosylate, with amines of the general formula (V)

(V)

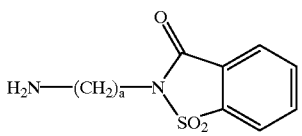

in which a has the meaning indicated above, in inert solvents, if appropriate in the presence of a base and/or of a catalyst, or

[C] reacting compounds of the general formula (VI)

(VI)

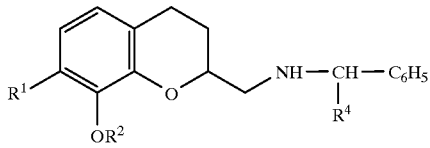

in which

R$^1$ and R$^2$ have the meaning indicated above, and

R$^4$ represents hydrogen or methyl, first either with formaldehyde or formaldehyde derivatives and compounds of the general formula (VII)

(VII)

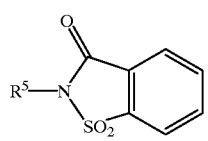

in which

R$^5$ represents a radical of the formula $HC\equiv C-(CH_2)_b-$, in which b denotes a number 0, 1 or 2, in a Mannich-analogous reaction and then hydrogenating.

The processes according to the invention can be illustrated by way of example by the following reaction scheme:

[A]

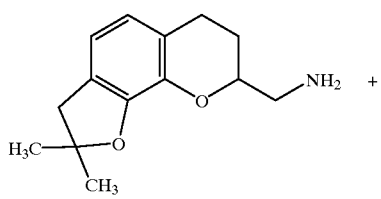

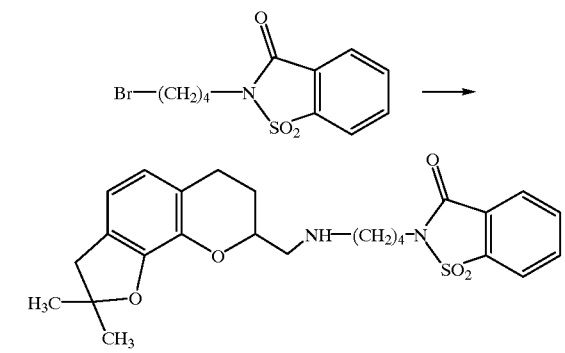

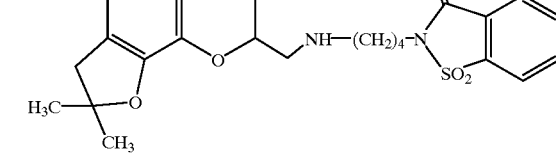

[B]

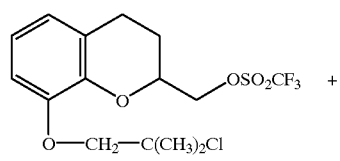

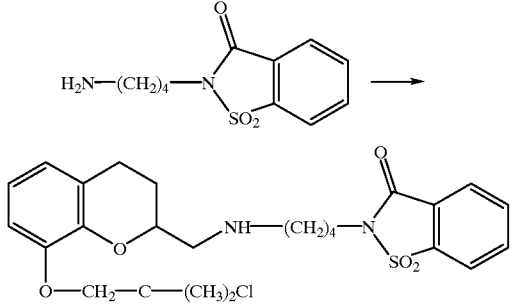

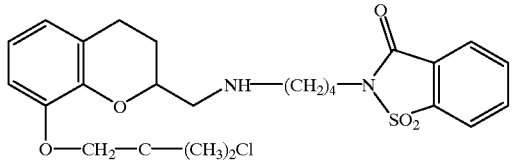

-continued

[C]

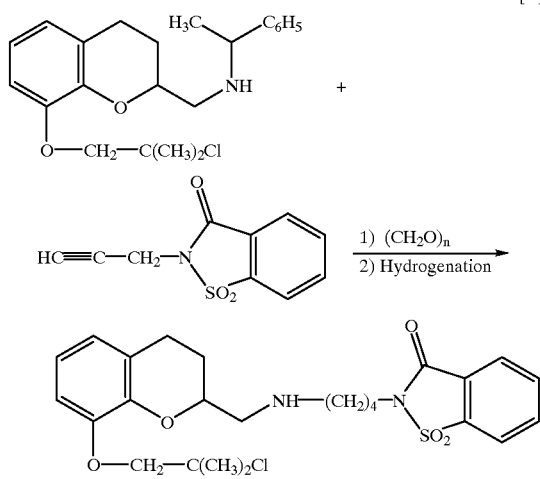

Suitable solvents for processes [A] and [B] are the customary solvents which do not change under the reaction conditions. These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoramide, or dimethyl sulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used. Methanol, ethanol, isopropanol, dimethylformamide and acetonitrile are preferred.

Suitable bases are the customary inorganic or organic bases. These preferably include alkali metal hydroxides such as sodium or potassium hydroxide, or alkali metal carbonates such as sodium or potassium carbonate, or alkali metal alkoxides such as sodium or potassium methoxide, or sodium or potassium ethoxide, or organic amines such as triethylamine, pyridine, picoline or N-methylpiperidine, or amides such as sodium amide or lithium diisopropylamide, or organometallic compounds such as butyllithium or phenyllithium. Sodium and potassium carbonate, pyridine and triethylamine are preferred.

The reactions [A] and [B] can in general be carried out in a temperature range from −20° C. up to the reflux temperature of the solvent, preferably from +20° C. up to the reflux temperature of the solvent.

Processes [A] and [B] are in general carried out at normal pressure. However, it is also possible to carry out the reaction at elevated or reduced pressure.

Reaction accelerators employed are in general alkali metal iodides; sodium iodide or potassium iodide is preferred.

The base is in this case employed in an amount from 1 to 5, preferably from 1 to 2, mol, based on 1 mol of the compounds of the general formulae (II) and (V).

The reaction with formaldehyde and acetylene derivatives in a Mannich-like reaction is in general carried out in one of the abovementioned organic solvents which do not change under the particular reaction conditions, such as alcohols, ethers, hydrocarbons, halogenohydrocarbons and dimethylformamide as well as their mixtures. Tetrahydrofuran and 1,4-dioxane are preferred.

In general, the catalysts employed are Copper salts. Copper(II) acetate is preferred. Paraformaldehyde, trioxane, formalin solution and gaseous formaldehyde are used as the formaldehyde source. Paraformaldehyde is preferred.

The reaction is in general carried out in a temperature range from 0° C. up to the reflux temperature, preferably from +20° C. to +70° C.

The reaction can be carried out at normal, elevated or at reduced pressure (e.g. 0.5 to 5 bar). In general, the reaction is carried out at normal pressure.

The hydrogenation (process C) is in general carried out with hydrogen in water or one of the abovementioned solvents, preferably water, methanol, ethanol, diethyl ether or tetrahydrofuran in the presence of mineral acids such as hydrochloric acid. Suitable catalysts are catalysts such as Raney nickel, palladium, palladium on animal carbon or platinum, preferably palladium and palladium on animal carbon.

The catalyst is employed in an amount from 0.01 mol to 0.2 mol, preferably from 0.05 mol to 0.15 mol, in each case relative to the blocked compounds of the general formula (IIa).

The reaction can be carried out at normal, elevated or at reduced pressure (e.g. 0.5 to 25 bar). In general, the reaction is carried out at normal pressure to 3 bar.

The compounds of the general formula (II) are new and can be prepared, for example, by converting compounds of the general formula (VIII)

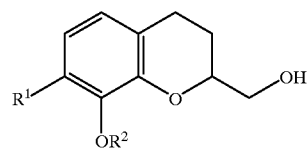

(VIII)

in which $R^1$ and $R^2$ have the meaning indicated above, first with phthalimide in the presence of triphenylphosphane/diethyl azodicarboxylate in one of the abovementioned solvents, preferably tetrahydrofuran, into the compounds of the general formula (IX)

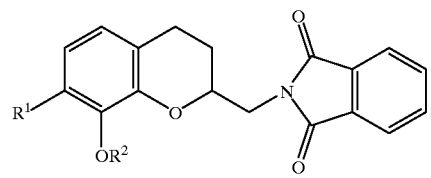

(IX)

in which $R^1$ and $R^2$ have the meaning indicated above, and in a second step removing the phthalimide group in aminoethanol.

The various reaction steps proceed in a temperature range from 0° C. to +100° C., preferably from room temperature to +80° C. and at normal pressure.

The compounds of the general formula (IX) are new and can be prepared, for example, as described above.

The compounds of the general formula (VIII) are new and can be prepared, for example, by alkylating 8-hydroxy-2-hydroxymethylchroman of the formula (X)

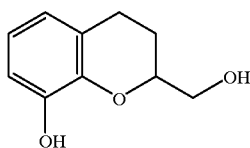

with compounds of the general formula (XI)

$$R^6\text{—}Y \quad (XI)$$

in which $R^6$ denotes straight-chain or branched alkyl or alkenyl having up to 4 carbon atoms, and Y represents halogen, preferably chlorine, bromine or iodine, and if appropriate in a second step introducing the radicals mentioned above under $R^1$ and $R^2$ by derivatization according to customary methods.

Derivatizations in the context of the invention are, for example, hydrochlorination with HCl in dioxane, rearrangement in the presence of N-methylpyrrolidone under a protective gas atmosphere and cyclization using formic acid.

The compound of the formula (X) is new and can be prepared from the known 8-methoxy-2-hydroxymethylchroman by reaction with HBr [cf. for this EP 352 613].

The compounds of the general formula (XI) are known.

The compounds of the general formula (VI) are new and can be prepared, for example, by reacting the compounds of the general formula (IV) mentioned above with amines of the general formula (XII)

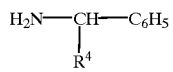

in which $R^4$ has the meaning indicated above, in the presence of sodium iodide in a temperature range from +50° C. to +150° C., preferably at 100° C. and normal pressure.

The amines of the general formula (XII) are known.

The compounds of the general formula (IV) are new as a species and can be prepared, for example, by reacting the abovementioned compounds of the general formula (VIII) with compounds of the general formula (XIII)

$$R^3\text{—}X \quad (XIII)$$

in which $R^3$ has the meaning indicated above, and

X represents halogen, preferably chlorine, in one of the abovementioned solvents, preferably pyridine, in a temperature range from 0° C. to room to preferably at room temperature and normal pressure.

The compounds of the general formula (XIII) are known.

The compounds of the general formulae (III), (V) and (VII) are known per se or can be prepared by customary methods.

The compounds according to the invention can be used as active compounds in medicaments. The substances according to the invention have a particularly high affinity for cerebral 5-hydroxy-tryptamine receptors of the 5-$HT_1$ type.

Surprisingly, the compounds according to the invention show low dependence in their metabolization of liver enzymes of the type CYP 2D6.

The compounds described in the present invention are thus active compounds for the control of illnesses which are characterized by disorders of the serotoninergic system, in particular in involvement of receptors which have high affinity for 5-hydroxytryptamine (5-$HT_1$ type). They are therefore suitable for the treatment of disorders of the central nervous system such as states of anxiety, tension and depression, central nervous system-related sexual dysfunctions and sleep disorders, and for the regulation of pathological disorders of the absorption of foodstuffs, luxury foods and addictive drugs. They are furthermore suitable for the elimination of cognitive deficits, for the improvement of learning and memory disorders and for the treatment of Alzheimer's disease.

Furthermore, these active compounds are also suitable for the modulation of the cardiovascular system. They also intervene in the regulation of the cerebral circulation and are thus effective agents for the control of migraine. They are also suitable for the prophylaxis and control of the sequelae of cerebral infarct (apoplexia cerebri) such as stroke, cerebral ischaemias and of craniocerebral trauma. The compounds according to the invention can also be employed for the control of states of pain. They are also suitable for the control of disorders of the immune system.

1) Affinity for the 5-$HT_1$ receptor

Table A shows by way of example the high affinity of the compounds according to the invention for 5-hydroxytryptamine receptors of the subtype 1. The values indicated are data which were determined from receptor binding studies using calf hippocampus membrane preparations. The radiolabelled ligand used for this purpose was $^3$H-serotonin.

TABLE A

| Compound of Example | $K_i$ (nmol/l) |
|---|---|
| 1 | 1.1 |
| 4 | 2.8 |
| 5 | 0.5 |

2.) Affinity for the 5-$HT_{1A}$ receptor [W. U. Dompert et al., Naunyn-Schmiedeberg's Arch Pharmacol. (1985), 328, 467–470].

In this test, the binding of $^3$H-ipsapirone to 5-$HT_{1A}$ receptors is measured in calf hippocampus membranes. It was found that the compounds according to the invention compete with the radioligand for binding and inhibit this.

TABLE B

| Compound of Example | $K_i$ (nmol/l) |
|---|---|
| 2 | 0.5 |
| 3 | 1.8 |
| 6 | 0.9 |

In the binding tests under 1) and 2), $IC_{50}$ values are determined which indicate at which concentration of test substance 50% of the binding of the radioligand is displaced. Taking into account the dissociation constants and the concentration of radioligand, the inhibition constants $K_i$ are calculated from this.

3.) Activity in animal models

Animal model: permanent focal cerebral ischaemia ("middle cerebral artery occlusion"=MCA-O). MCA occlusion in rodents is a widely accepted animal model of stroke. Reference: Bederson, J. B. et al., Stroke, 17:472–476 (1986).

In order to produce permanent focal cerebral ischaemia, the left medial cerebral artery in rats is occluded by electrocoagulation. The resulting infarct volume in cortical (subcortical) regions which are supplied by the medial cerebral artery is used as a measure of the extent of the stroke-induced neuronal damage. Administration of substance: after occlusion as a continuous i.v. infusion (4 hours) of the test substance, beginning directly after operation. The animals are sacrificed for assessment 7 days after operation.

Results:

| Example | % Reduction of the infarct volume | Dose: mg/kg i.v. |
|---|---|---|
| 2 | 36 | 0.001 |
|  | 48 | 0.01 |
|  | 32 | 0.1 |
| 6 | 41 | 0.001 |
|  | 41 | 0.01 |
|  | 38 | 0.1 |
| 3 | 37 | 0.001 |
|  | 34 | 0.003 |
|  | 47 | 0.01 |
| for comparison: | (increase by 21%) | 0.1 |
| Ex. 86 from | 15 | 1.0 |
| EP 352 613* | 1 | 3.0 |

*: MCA-O mouse, substance administration directly as a bolus injection, 2 and 4 hours after occlusion; sacrifice after 2 days 4.) Stability in human liver microsomes with and without addition of quinidine.

In order to determine the extent of cytochrome P-450 (CYP) 2D6-dependent biotransformation, the phase I metabolism of human liver microsomes was investigated with and without addition of quinidine, a selective inhibitor of CYP 2D6. The areas under the concentration time courses ($AUC_{norm}$) and the half-lives were determined.

In the case of the compounds of Example 2, Example 3 and Example 6, the $AUC_{norm}$ increases after addition of quinidine and the half-life increases after addition of quinidine by the factor 1.3 to 2.0, while in Example 93.i from EP 352 613 and Ex. 4 from EP 540 914 an increase by the factor 4 in $AUC_{norm}$ and half-life is to be observed.

The compounds according to the invention advantageously show a lower dependence on the phase I metabolism via the CYP 2D6 enzyme than known chromans.

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight, of the total mixture.

In addition to the active compounds of the formula (I), the pharmaceutical preparations can also contain other pharmaceutical active compounds.

The abovementioned pharmaceutical preparations can be prepared by known methods in a customary manner, for example using the auxiliary(ies) or excipient(s).

In general, it has proved advantageous to administer the active compounds of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, if appropriate it can be advantageous to deviate from the amounts mentioned, namely depending on the species and on the body weight of the subject treated, on the individual behaviour towards the medicament, the nature and severity of the disorder, the type of preparation and administration, and the time or interval at which administration takes place.

Starting compounds

EXAMPLE I (−)-8-Hydroxy-2-hydroxymethylchroman

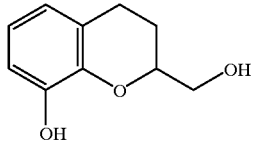

135.5 g (0.7 mol) of (−)-2-hydroxymethyl-8-methoxychroman are heated in 0.7 l of 48% strength aqueous HBr solution for 20 hours. After cooling and diluting with 1.2 l of ice water, the mixture is stirred for 30 minutes and the deposited precipitate is filtered off with suction. Washing with ice-water and drying over phosphorus pentoxide yields 109.5 g (87%) of the title compound, m.p. 131–132° C.

$\alpha_{289}^{20} = -133.8$ (c=0.7, methanol)

EXAMPLE II

2-Hydroxymethyl-8-isopropoxy-chroman

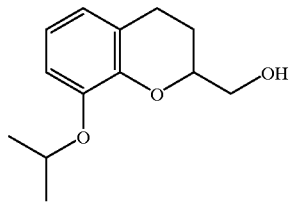

4.5 g (25 mmol) of 8-hydroxy-2-hydroxymethyl-chroman, 4.6 g (27 mmol) of 2-iodopropane and 5.2 g (37.5 mmol) of powdered potassium carbonate in 50 ml of dimethylformamide are heated at 60° C. for 40 hours. After addition of a further 0.9 g of iodopropane, the mixture is heated at 80° C. for 24 hours and then at 95° C. for a further 24 hours. After cooling, it is partitioned between toluene and water and filtered through Celite®. The organic phase is dried (magnesium sulphate) and concentrated. After flash chromatography (silica gel; elusion with toluene/ethyl acetate gradients 3:1– 2:1), 7 g of crude product are obtained which is purified by chromatography on silica gel (gradient toluene/ethyl acetate 1:0–8:1). Yield: 2.9 g (52%) of oil. $R_F$ (silica gel, toluene/ethyl acetate 1:1): 0.4

EXAMPLE III (−)-2-Hydroxymethyl-8-isopropoxy-chroman

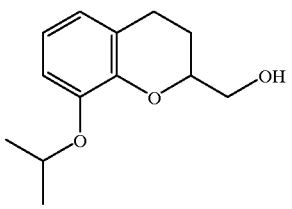

The title compound is obtained from the compound of Example I in analogy to the procedure of Example II.

$\alpha_{289}^{20} = -85$ [c=0.5, CHCl$_3$]

EXAMPLE IV

2-Hydroxymethyl-8-(2-methyl-propen-2-yloxy)chroman

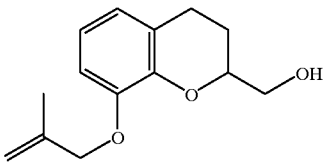

0.9 g (5 mmol) of 8-hydroxy-2-hydroxymethyl-chroman, 0.5 g (5.5 mmol) of 3-chloro-2-methylpropene, 0.02 g of sodium iodide and 1.0 g (7.5 mmol) of powdered potassium carbonate are heated at 90° C. for 3 hours in 10 ml of dimethylformamide. After cooling, the mixture is partitioned between water and toluene. The toluene phase is purified by flash chromatography on silica gel (toluene/ethyl acetate). 1.3 g (100%=1.2 g) of crude product are thus obtained, which is reacted further. $R_F$ (silica gel, toluene/ethyl acetate 1:1): 0.45

EXAMPLE V (−)-2-Hydroxymethyl-8-(2-methyl-propen-2-yloxy) chroman

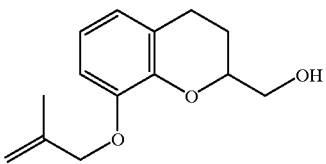

The title compound from Example I is obtained in analogy to the procedure of Example IV.

$\alpha_{289}^{20} = -87$ [c=0.5, CHCl$_3$]

EXAMPLE VI

2-Hydroxymethyl-8-(2-chloro-2-methyl-propoxy) chroman

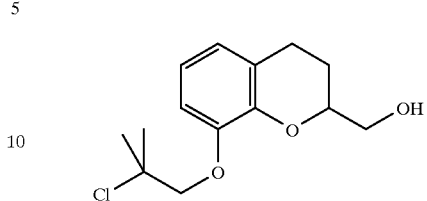

12.5 g (53.4 mmol) of the compound from Example IV are heated at 55° C. for 6 hours in 4N hydrochloric acid in dioxane. After concentrating, the residue is purified by flash chromatography on silica gel (toluene-ethyl acetate 1:0–20:1). 4.0 g of the title compound are thus obtained as an oil. Using toluene/ethyl acetate, 4.0 g (42%) of unreacted starting material are recovered.

$^1$H-NMR (CDCl$_3$, δ values in ppm): 1.7 (s; 6H), 1.7–2.1 (m, 2H), 2.6 (bs; 1H), 2.7–3.0 (m; 2H), 3.7–3.9 (m, 2H), 4.0 (s; 2H), 4.05–4.15 (m; 1H), 6.65–6.8 (m, 3H).

EXAMPLE VII (−)-2-Hydroxymethyl-8-(2-chloro-2-methyl-propoxy) chroman

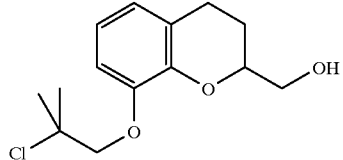

Obtainable from Ex. V analogously to Example VI; $\alpha_{289}^{20} = -70$ [c=0.4 CHCl$_3$]

EXAMPLE VIII

8-Hydroxy-2-hydroxymethyl-7-(2-methyl-propen-2-yl) chroman

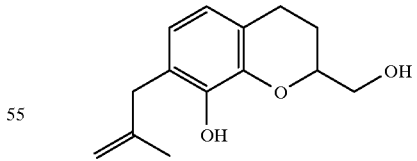

1.3 g (5 mmol) of compound from Example IV are dissolved in 4 ml of N-methylpyrrolidone and heated at 210° C. for 4 hours under argon. After cooling the mixture is filtered through silica gel (toluene/ethyl acetate mixtures). The eluates are concentrated and partitioned between diethyl ether and water. After drying (magnesium sulphate) and concentrating, 1.0 g (77%) of crude product is obtained as an oil which is directly reacted further.

EXAMPLE IX (−)-8-Hydroxy-2-hydroxymethyl-7-(2-methyl-propen-2-yl)chroman

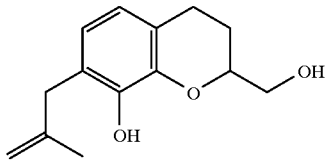

The title compound from Example V is obtained in analogy to the procedure of Example VIII.

$\alpha_{289}^{20} = -88$ [c=1, CHCl$_3$]

EXAMPLE X 2,2-Dimethyl-3,6,7,8-tetrahydro-2H-1,9-dioxa-cyclopenta[a]naphthalen-8-yl-methanol

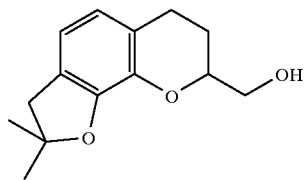

1.0 g (4 mmol) of compound from Example VIII is heated to reflux for 2 hours in 3 ml of formic acid. After concentrating, the mixture is treated with 10 ml of 20% potassium hydroxide and heated to reflux for 1 hour. After cooling, the mixture is acidified with hydrochloric acid and extracted with ethyl acetate. The organic phase is dried (magnesium sulphate) and concentrated. Flash chromatography on silica gel (elution with toluene/ethyl acetate gradients 1:0–3:1) affords 0.73 g (78%) of the title compound as a syrup.

$^1$H-NMR (CHCl$_3$, δ values in ppm): 1.5 (s; 6H), 1.9–2.1 (m; 2H), 2.7–2.9 (m; 2H), 3.0 ("s"; 2H), 3.7–4.0 (m; 2H), 4.1–4.2 (m; 1H), 6.4–6.7 (AB system; 2H)

EXAMPLE XI (−)-2,2-Dimethyl-3,6,7,8-tetrahydro-2H-1,9-dioxa-cyclopenta[a]naphthalene-8-yl-methanol

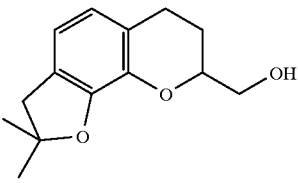

The title compound from Example IX is obtained in analogy to the procedure of Example X $\alpha_{289}^{20} = -87$ [c=0.5, CHCl$_3$]

EXAMPLE XII 8-(2-Chloro-2-methyl-propoxy)-2-(phthalimidomethyl)chroman

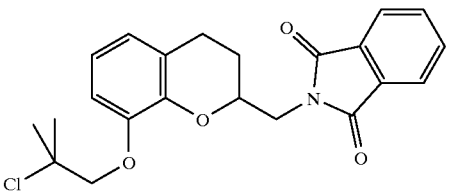

3.3 g (18.5 mmol) of diethyl azodicarboxylate in 15 ml of tetrahydrofuran are slowly added dropwise at room temperature and with exclusion of light to 4.0 g (17 mmol) of a compound from Example VI, 4.9 g (18.5 mmol) of triphenylphosphane and 2.7 g (18.5 mmol) of phthalimide in 40 ml of tetrahydrofuran. After 1 hour at room temperature, the mixture is concentrated and the residue is purified by flash chromatography (cyclohexane/ethyl acetate gradients 1:0–20:1).

R$_F$ (toluene/ethyl acetate 3:1): 0.27

The compounds listed in Table 1 can be obtained in analogy to Example XII.

TABLE I

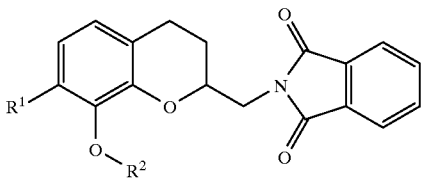

| Ex. No. | R$^1$ | R$^2$ | Enantiomer | Data | Prepared from Example |
|---|---|---|---|---|---|
| XIII | H | —CH(CH$_3$)$_2$ | (−)-Enantiomer | $\alpha_{289}^{20} = -39$ [c = 0.6, CHCl$_3$] | III |
| XIV | H | —CH(CH$_3$)$_2$ | Racemate | R$_f$ (toluene/ethyl acetate 3:1): 0.6 | II |
| XV | H | CH$_2$—C(CH$_3$)$_2$Cl | (−)-Enantiomer | $\alpha_{289}^{20} = -21$ [c = 0.7, CHCl$_3$] | VII |
| XVI | —CH$_2$—C(CH$_3$)$_2$— | | Racemate | | X |

TABLE I-continued

[Structure: chroman with R¹ at 7-position, O-R² at 8-position, and CH₂-phthalimide at 2-position]

| Ex. No. | R¹ | R² | Enantiomer | Data | Prepared from Example |
|---|---|---|---|---|---|
| XVII | | —CH₂—C(CH₂)₂— | (−)-Enantiomer | $\alpha_{289}^{20}$ = −90.2 [c = 1, CHCl₃] | XI |

EXAMPLE XVIII

2-Aminomethyl-8-(2-chloro-2-methyl-propoxy)chroman

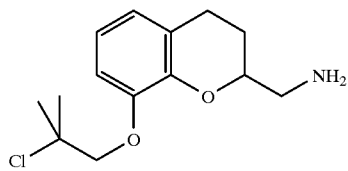

5.8 g (14.5 mmol) of the compound from Example XII are heated at 80° C. for 30 minutes with 13.4 g (220 mmol) of aminoethanol. After cooling, the mixture is diluted with water and extracted with ethyl acetate. Drying the organic phase and concentrating yields a crude product which is purified by flash chromatography on silica gel (elution with toluene-isopropanol gradients 1:0 to 1:1, addition of 1% triethylamine). 3.35 g (86%) of title compound are thus obtained as an oil. $R_F$ (dichloromethane/methanol 10:1): 0.15

The compounds listed in Table 2 can be obtained in analogy to Example XVIII.

EXAMPLE XXIV (−)-8-Isopropoxy-2-mesyloxymethyl-chroman

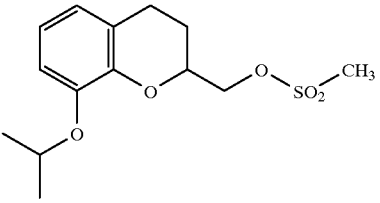

68 g (0.6 mol) of methanesulphonyl chloride are added dropwise at room temperature to 114 g (0.51 mol) of the compound from Example III in 95 g of pyridine. After stirring at room temperature for 18 hours, the mixture is diluted with 700 ml of water and extracted with dichloromethane. Filtration through silica gel and concentration affords 150 g of crude product which is purified by crystallization from 1.5 l of cyclohexane/toluene mixture 3:1. The mother liquor is recrystallized after concentrating from cyclohexane. A total of 112 g of title compound are thus obtained as a colourless solid, m.p. 77–78° C.

$\alpha_{289}^{20}$=−56.2 [c=0.9, CH₃OH]

TABLE II

[Structure: chroman with R¹ at 7-position, O-R² at 8-position, CH₂-NH at 2-position]

| Ex. No. | R¹ | R² | Enantiomer | Data | Prepared from Example |
|---|---|---|---|---|---|
| XIX | H | —CH(CH₃)₂ | Racemate | $R_f$ (Tol/iProH): = 0.15; reacted further in crude form | XIV |
| XX | H | —CH(CH₃)₂ | Enantiomer | TLC identical to Ex. XIX; reacted further in crude form | XIII |
| XXI | H | —CH₂—C(CH₃)₂Cl | Enantiomer | TLC identical to Ex. XVIII, reacted further in crude form | XV |
| XXII | | —CH₂—C(CH₃)₂— | Racemate | | XVI |
| XXIII | | —CH₂C(CH₃)₂— | Enantiomer | TLC identical to Ex. XXII; reacted further in crude form | XVII |

EXAMPLE XXV (−)-2-Benzylaminomethyl-8-isopropoxy-chroman

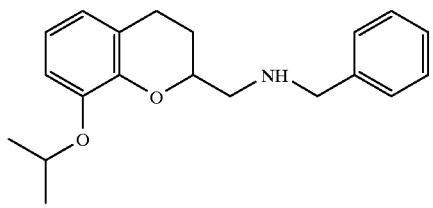

112 g (0.37 mol) of the compound from Example XXIV, 200 g (1.87 mol) of benzylamine and 3.0 g (0.02 mol) of sodium iodide are heated at 100° C. for 5 hours. After cooling, the solid is separated off and the organic phase is washed twice with 2.5 l of water each time. The residual oil is taken up with 1 l of ethyl acetate. Washing the ethyl acetate phase with water and saturated sodium chloride solution and subsequent drying and concentration affords 114.5 g (quant) of the title compound (HPLC purity: 93%) as an oil which is employed in the next step.

$\alpha_{289}^{20}=-104$ [c=0.5, CH$_3$OH]

EXAMPLE XXVI (−)-2-(N-Benzyl-N-(4-(1,1-dioxido-3-oxo-2,3-dihydro-benzisothiazol-2-yl)-2-butinyl)-aminomethyl)-8-isopropoxy-chroman hydrochloride

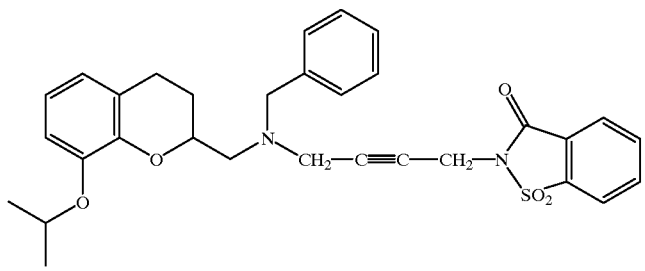

114 g (0.37 mol) of the compound from Example XXV and 13.5 g (0.45 mol) of paraformaldehyde in 1 l of dioxane are treated with 4 g of copper(II) acetate and heated to 50° C. 81 g (0.37 mol) of propargylsaccharin are added at this temperature. After stirring at 80° C. for 2 hours, the mixture is concentrated and the residue is partitioned between toluene/water with addition of Tonsil. After filtration of the mixture through Celite®, the organic phase is separated off and purified by flash chromatography on silica gel (toluene/ethyl acetate 10:1). Precipitation of the hydrochloride from ether using ethereal hydrochloric acid affords 226 g of crude product. After liberation of the free base with sodium hydrogen carbonate, this product is purified by chromatography on silica gel (elution with toluene/ethyl acetate 20:1). The product fractions are treated with ethereal hydrochloric acid. 139 g (65%) of title compound are thus obtained as a solid, m.p. 106–109° C.

$\alpha_{289}^{20}=-64.1$ [c=0.8, CH$_3$OH]

PREPARATION EXAMPLES

Example 1

2-(N-(4-(1,1-Dioxido-3-oxo-2,3-dihydro-benzisothiazol-2-yl)butyl)amino)methyl-8-isopropoxy-chroman oxalate

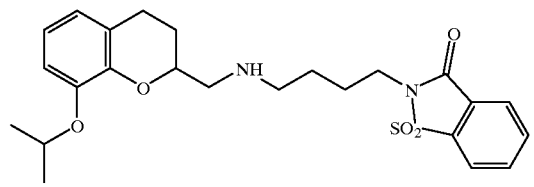

2.7 g (12 mmol) of the compound from Example XIX are dissolved in 35 ml of dimethylformamide and treated with 3.4 g (10.5 mmol) of 4-bromobutylsaccharin and 2.5 g (25 mmol) of triethylamine. After addition of 50 mg of potassium iodide, the mixture is stirred at 50° C. for 15 hours. The reaction mixture is diluted with water and extracted several times with toluene. The organic phase is dried and concentrated Chromatography twice using toluene-ethyl acetate gradients affords 3.0 g of crude product (free base). Using oxalic acid in ethanol precipitates the oxalate, which is recrystallized from water. 2.4 g of oxalate are thus obtained, m.p. 179–180° C.

Elemental analysis: $C_{24} H_{30} N_2 O_5 S \times C_2 H_2 O_4 \times 0.5 H_2O$
calc.: C: 56.0 H: 5.9 N: 5.0 O: 27.3 found: C: 55.8 H: 6.1 N: 5.0 O: 27.1

The compounds listed in Table 1 can be obtained in analogy to Example 1.

TABLE 1

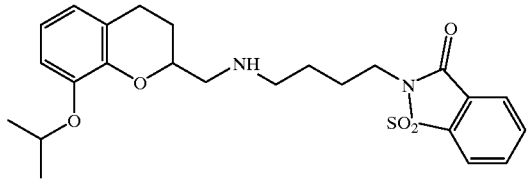

| Ex. No. | R¹ | R² | Enantiomer | Data | Prepared from |
|---|---|---|---|---|---|
| 2 | H | —CH(CH$_3$)$_2$ | (–)-Enantiomer | Oxalate: m.p. 202° C. (from isopropanol); $\alpha_{289}^{20}$ = –57.7 [c = 1, CH$_3$OH]; Analysis: C$_{24}$H$_{30}$N$_2$O$_5$S × HCl | XX |
| 3 | H | —CH$_2$—C(CH$_3$)$_2$Cl | (–)-Enantiomer | Hydrochloride: m.p. 155–157° C. (from ether/isopropanol) $\alpha_{289}^{20}$ = –44.7 [c = 1, CH$_3$OH] | XXI |
| 4 | H | —CH$_2$—C(CH$_3$)$_2$Cl | Racemate | Hydrochloride: m.p. 181° C. (from ether/isopropanol) | XVIII |
| 5 | —CH$_2$C(CH$_3$)$_2$— | | Racemate | Hydrochloride: m.p. 174–176° C. (from ether/isopropanol) | XXII |
| 6 | —CH$_2$C(CH$_3$)$_2$— | | (–)-Enantiomer | Hydrochloride: m.p. 210° C. $\alpha_{289}^{20}$ = –71.3 [c = 1, CH$_3$OH] | XXIII |

Example 7

(–)-2-(N-(4-(1,1-Dioxido-3-oxo-2,3-dihydro-benzisothiazol-2-yl)butyl)amino)methyl-8-isopropoxy-chroman hydrochloride

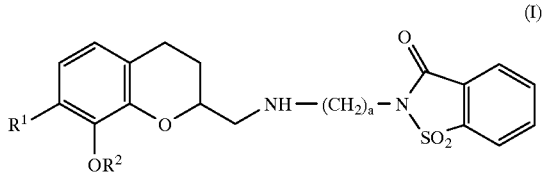

120 g (0.21 mmol) of the compound from Example XXVI in 1.4 l of methanol are treated with 400 ml of conc. hydrochloric acid and 20 g of 10% palladium on active carbon. After hydrogenating at normal pressure and 20° C. for 4 hours, the catalyst is filtered off and the filtrate is concentrated. The residue is concentrated twice with toluene and dissolved using 400 ml of ethyl acetate. Addition of 800 ml of diethyl ether and stirring at room tempera for 18 h affords 90.5 g of solid after filtering off with suction and drying in vacuo. Recrystallization from 1 l of acetonitrile and washing the crystals with diethyl ether affords 70.8 g (69%) of title compound as colourless crystals, m.p. 153–154° C.

$\alpha_{289}^{20}$ = –65.9 [c=0.6, CH$_3$OH]

Elemental analysis: C$_{24}$ H$_{30}$ N$_2$ O$_5$ S×HCl Calc.: C: 58.2 H: 6.3 N: 5.7 O: 16.2 Cl: 7.2 S: 6.5 Found: C: 58.0 H:6.3 N: 5.7 O: 16.2 Cl: 7.1 S: 6.3

We claim:

1. A benzisothiazolyl-substituted aminomethylchroman compound of the formula (I)

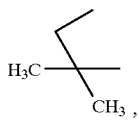
(I)

in which

R$^1$ represents hydrogen, and
R$^2$ represents a radical of the formula —CH(CH)$_2$ or —CH$_2$—C(CH$_3$)$_2$—Cl, or
R$^1$ and R$^2$ together form a radical of the formula

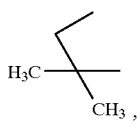

and
a represents a number 4 or 5,
a stereoisomer thereof, or a physiologically acceptable salt of said compound or said stereoisomer.

2. A benzisothiazolyl-substituted aminomethylchroman compound according to claim 1, in which R$^1$ represents hydrogen, and
R$^2$ represents a radical of the formula —CH(CH$_3$)$_2$ or —CH$_2$—C(CH$_3$)$_2$—Cl, or
R$^1$ and R$^2$ together form a radical of the formula

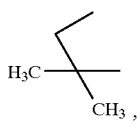

and
a represents a number 4, a stereoisomer thereof, or a physiologically acceptable salt of said compound or said stereoisomer.

3. A benzisothiazolyl-substituted aminomethylchroman compound according to claim 1, in which $R^1$ represents hydrogen, and $R^2$ represents a radical of the formula —CH(CH$_3$)$_2$ or —CH$_2$—C(CH$_3$)$_2$—Cl, or $R^1$ and $R^2$ together form a radical of the formula

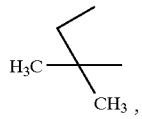

and a represents the number 4, a stereoisomer thereof, or a physiologically acceptable salt of said compound or said stereoisomer.

4. A benzisothiazolyl-substituted aminomethylchroman compound according to claim 1 wherein such compound is the oxalate of 2-(N-(4-(1,1-Dioxido-3-oxo-2,3-dihydro-benzisothiazol-2-yl)butyl)amino)methyl-8-isopropoxy-chroman of the formula

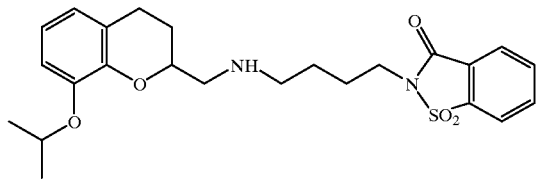

a stereoisomer thereof, or a physiologically acceptable salt of said compound or said stereoisomer.

5. A composition for treating an illness characterized by a disorder of the serotoninergic system in a patient suffering therefrom, said composition comprising an amount of a compound, stereoisomer or salt thereof according to claim 1 which is effective to treat said illness and a pharmacologically acceptable diluent.

6. A method of treating an illness characterized by a disorder of the serotoninergic system in a patient suffering therefrom comprising administering to said patient an amount of a compound, stereoisomer or salt thereof according to claim 1 which is effective to treat said illness.

* * * * *

UNITED STATES PATENT AND TRADEMARK OFFICE
CERTIFICATE OF CORRECTION

PATENT NO.     : 5,942,529
DATED          : August 24, 1999
INVENTOR(S)    : Schohe-Loop et al.

It is certified that error appears in the above-identified patent and that said Letters Patent is hereby corrected as shown below:

Column 20,
Line 38, "of the formula – $CH(CH)_2$" should read -- $CH(CH_3)_2$ --

Signed and Sealed this

Second Day of November, 2004

JON W. DUDAS
*Director of the United States Patent and Trademark Office*